United States Patent
Garfinkel et al.

(10) Patent No.: US 9,995,711 B2
(45) Date of Patent: Jun. 12, 2018

(54) CALIBRATION OF WEAR DETECTION SYSTEM

(75) Inventors: Michael Garfinkel, West Hartford, CT (US); Daryl J. Marvin, Farmington, CT (US)

(73) Assignee: OTIS ELEVATOR COMPANY, Farmington, CT (US)

( * ) Notice: Subject to any disclaimer, the term of this patent is extended or adjusted under 35 U.S.C. 154(b) by 806 days.

(21) Appl. No.: 14/389,409

(22) PCT Filed: Apr. 2, 2012

(86) PCT No.: PCT/US2012/031824
§ 371 (c)(1),
(2), (4) Date: Sep. 30, 2014

(87) PCT Pub. No.: WO2013/151525
PCT Pub. Date: Oct. 10, 2013

(65) Prior Publication Data
US 2015/0063415 A1 Mar. 5, 2015

(51) Int. Cl.
*G01N 27/61* (2006.01)
*G01R 35/00* (2006.01)
(Continued)

(52) U.S. Cl.
CPC .......... *G01N 27/61* (2013.01); *B66B 7/1223* (2013.01); *G01N 25/72* (2013.01); *G01N 27/20* (2013.01); *G01R 35/00* (2013.01)

(58) Field of Classification Search
CPC ........ G01N 27/04; G01N 27/20; G01N 27/61; G01N 25/72; G01R 35/00; B66B 7/1223
(Continued)

(56) References Cited

U.S. PATENT DOCUMENTS 5,212,982 A * 5/1993 Macchiarulo .......... G01N 27/20 324/700
5,307,672 A 5/1994 Macchiarulo et al.
(Continued)

FOREIGN PATENT DOCUMENTS

CN 1351710 A 5/2002
CN 1397797 A 2/2003
(Continued)

OTHER PUBLICATIONS

Notification of Transmittal of the International Search Report and the Written Opinion of the International Searching Authority, or the Declaration; PCT/US2012/031824; dated Dec. 12, 2012; 9 pages.
(Continued)

*Primary Examiner* — Peter Macchiarolo
*Assistant Examiner* — Anthony W Megna Fuentes
(74) *Attorney, Agent, or Firm* — Cantor Colburn LLP

(57) ABSTRACT

A method of wear detection of a coated belt or rope includes measuring an initial electrical resistance of one or more cords, strands or wires of the coated belt or rope. The initial electrical resistance is calibrated by repeating the measuring of initial electrical resistance and populating a database with the measured initial electrical resistance values. A true initial resistance is determined from the population of initial electrical resistances and subsequent measured values of electrical resistance of the one or more cords, strands or wires of the coated belt or rope.

10 Claims, 6 Drawing Sheets

(51) Int. Cl.
  *B66B 7/12* (2006.01)
  *G01N 27/20* (2006.01)
  *G01N 25/72* (2006.01)

(58) Field of Classification Search
  USPC ...... 374/142, 693; 187/391; 73/7, 9, 118.01, 73/158–160; 324/693, 691, 525, 601, 324/508–509
  See application file for complete search history.

(56) References Cited

U.S. PATENT DOCUMENTS

| | | | |
|---|---|---|---|
| 5,351,530 | A | 10/1994 | Macchiarulo et al. |
| 5,731,528 | A | 3/1998 | Yamazaki et al. |
| 6,289,742 | B1* | 9/2001 | De Angelis ............... B66B 7/06 73/158 |
| 7,409,870 | B2 | 8/2008 | Stucky et al. |
| 2005/0063449 | A1* | 3/2005 | Lustenberger ........ B66B 7/1223 374/4 |
| 2007/0180925 | A1 | 8/2007 | Stucky et al. |
| 2008/0223668 | A1* | 9/2008 | Stucky .................. B66B 7/1223 187/393 |
| 2010/0065729 | A1* | 3/2010 | Legras ...................... G01J 5/24 250/252.1 |
| 2011/0253487 | A1* | 10/2011 | Kocher ................. B66B 7/1223 187/393 |

FOREIGN PATENT DOCUMENTS

| | | |
|---|---|---|
| CN | 101484815 A | 7/2009 |
| EP | 2299251 A1 | 3/2011 |
| JP | 06286957 A | 10/1994 |
| JP | 4191529 B2 | 11/2004 |
| JP | 3700586 B2 | 9/2005 |
| SU | 1727045 A1 | 4/1992 |

OTHER PUBLICATIONS

State Intellectual Property Office of People's Republic China Search Report; Application No. 201280072248.8; dated Oct. 24, 2015; 2 pages.

Daxue Wuli Shiyan, CPEL1453811P, ISBN 978-7-5643-0475-1, Nov. 1, 2009, 7 pages. URL: http://press.swjtu.edu.cn, No English Translation.

Chinese Office Action Issued in CN Application No. 201280072248.8, dated Aug. 21, 2017, 6 Pages.

* cited by examiner

CALIBRATION OF WEAR DETECTION SYSTEM

BACKGROUND OF THE INVENTION

The subject matter disclosed herein relates to coated belts or ropes used, for example, in elevator systems. More specifically, the subject disclosure relates to wear detection (e.g. detection of corrosion, fretting, etc.) of coated belts or ropes used for elevator suspension and/or driving.

Elevator systems utilize ropes or belts operably connected to an elevator car, and routed over one or more sheaves, also known as pulleys, to propel the elevator car along a hoistway. Coated steel belts in particular include a plurality of wires located at least partially within a jacket material. The plurality of wires is often arranged into one or more strands and the strands are then arranged into one or more cords. In an exemplary belt construction, a plurality of cords is typically arranged equally spaced within a jacket in a longitudinal direction.

During normal elevator operation, coated steel belts are subjected to a large number of bending cycles as the belt travels over drive sheaves and deflector sheaves of the elevator system. These bending cycles cause a degradation of the breaking strength of the wires or cords within the coated steel belt via the mechanism of wire fretting or fatigue. Such fatigue is a major contributor to reduction in service life of the coated steel belt. While the service life of the coated steel belt can be estimated through calculation, a more accurate estimation of remaining life of the coated steel belt is often obtained by utilizing a life-monitoring system.

One such system is called resistance-based inspection (RBI). An RBI system is secured to the coated belt or rope at a fixed point of the elevator system and monitors a change in electrical resistance of one or more of the cords in the belt or rope. Since the electrical resistance of each cord is proportional to its cross-sectional area, changes is electrical resistance can be correlated to reduction in cross-sectional area of the cord, indicating an amount of fretting of the cord, and a corresponding remaining service life. The changes in electrical resistance are determined relative to a baseline resistance, typically taken at installation of the system. This initial reading compensates for cord temperature by measuring temperature at the monitoring unit, and then assumes the relationship between cord and monitoring unit temperature to be fixed over the life of the cord. Cord temperature has a significant effect on cord resistance, and therefore inaccuracy in cord temperature could lead to false alarms or false indications of adequate remaining cord life.

BRIEF DESCRIPTION OF THE INVENTION

According to one aspect of the invention, a method of wear detection of a coated belt or rope includes measuring an initial electrical resistance of one or more cords, strands or wires of the coated belt or rope. The initial electrical resistance is calibrated by repeating the measuring of initial electrical resistance and populating a database with the measured initial electrical resistance values. A true initial resistance is determined from the population of initial electrical resistances and subsequent measured values of electrical resistance of the one or more cords, strands or wires of the coated belt or rope.

Alternatively in this or other aspects of the invention, the true initial resistance is determined by computing an average of the population of initial electrical resistances.

Alternatively in this or other aspects of the invention, the initial resistance measurement is repeated hourly.

Alternatively in this or other aspects of the invention, the initial resistance measurement is repeated over a period of about six months.

Alternatively in this or other aspects of the invention, the method further includes measuring an initial belt temperature at the time of measuring the initial electrical resistance one or more cords, strands or wires of the coated belt or rope and repeating the initial temperature measurement along with repeating the measuring of initial resistance. The database is populated with the measured initial temperatures correlated to the measured initial resistance values.

Alternatively in this or other aspects of the invention, electrical resistance of the one or more cords, strands or wires of the coated belt or rope and temperature are subsequently measured. The threshold is determined by using the measured temperature to determine the true initial electrical resistance at that measured temperature by querying the database and calculating the threshold as a percentage change from the true initial electrical resistance.

Alternatively in this or other aspects of the invention, action is taken if the threshold is exceeded.

According to another aspect of the invention, a monitoring system for a coated belt or rope having one or more cords, strands and/or wires includes a wear detection unit for engaging the one or more cords, strands or wire of the coated belt or rope and capable of measuring electrical resistance thereof and a temperature sensor capable of measuring temperature. A database is utilized to store electrical resistance and corresponding temperature measurements. The wear detection unit repeatedly measures an initial electrical resistance, and the temperature sensor repeatedly measures an initial temperature, the initial electrical resistance measurements and initial temperatures are utilized to determine a true initial electrical resistance.

The detailed description explains the invention, together with advantages and features, by way of examples with reference to the drawings.

DETAILED DESCRIPTION OF THE INVENTION

Figure 1A:
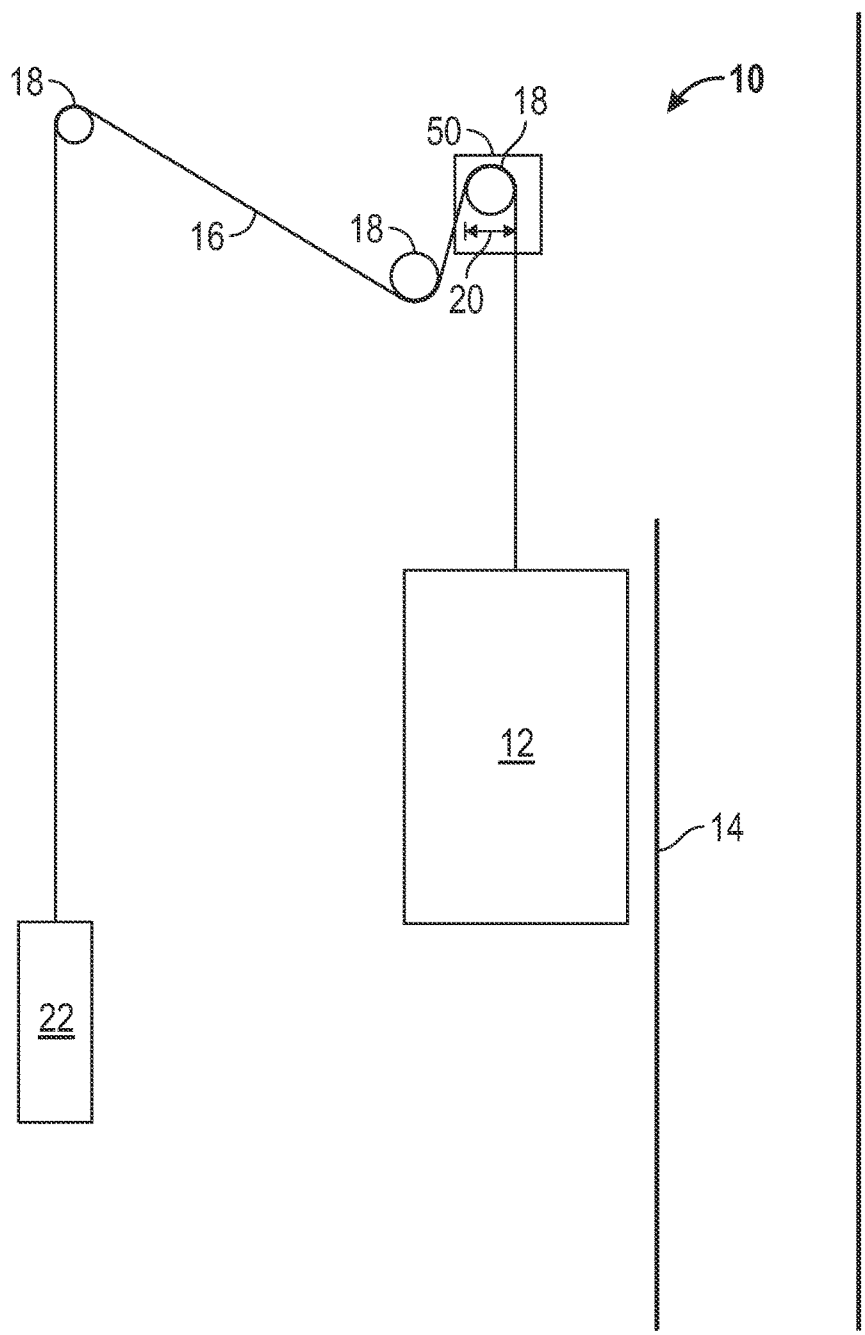
FIG. 1A is a schematic of an exemplary elevator system having a 1:1 roping arrangement.
Figure 1B:
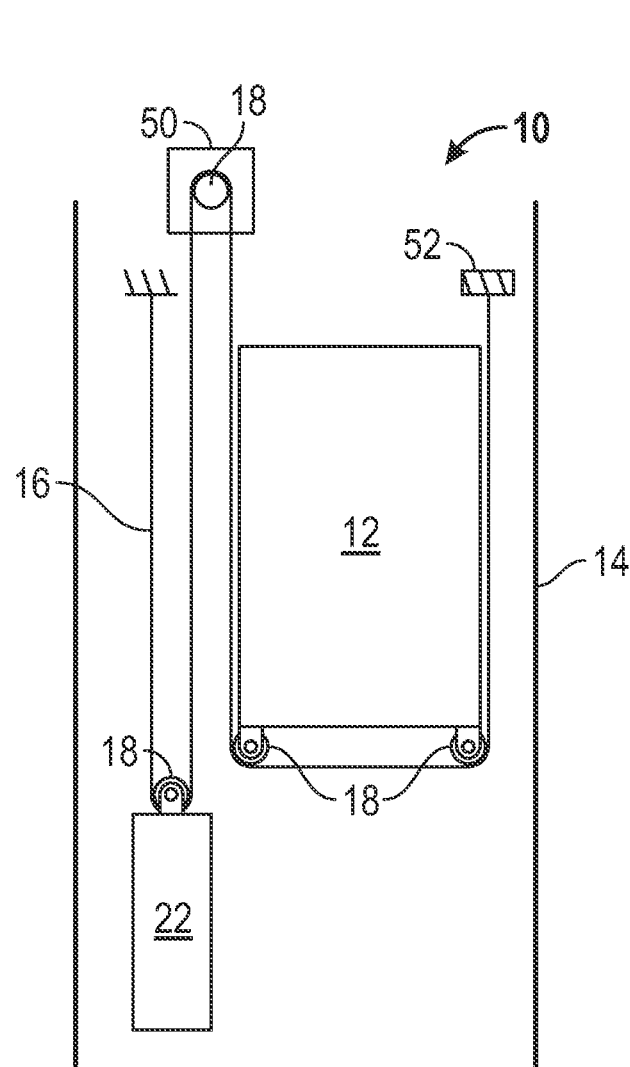
FIG. 1B is a schematic of another exemplary elevator system having a different roping arrangement.
Figure 1C:
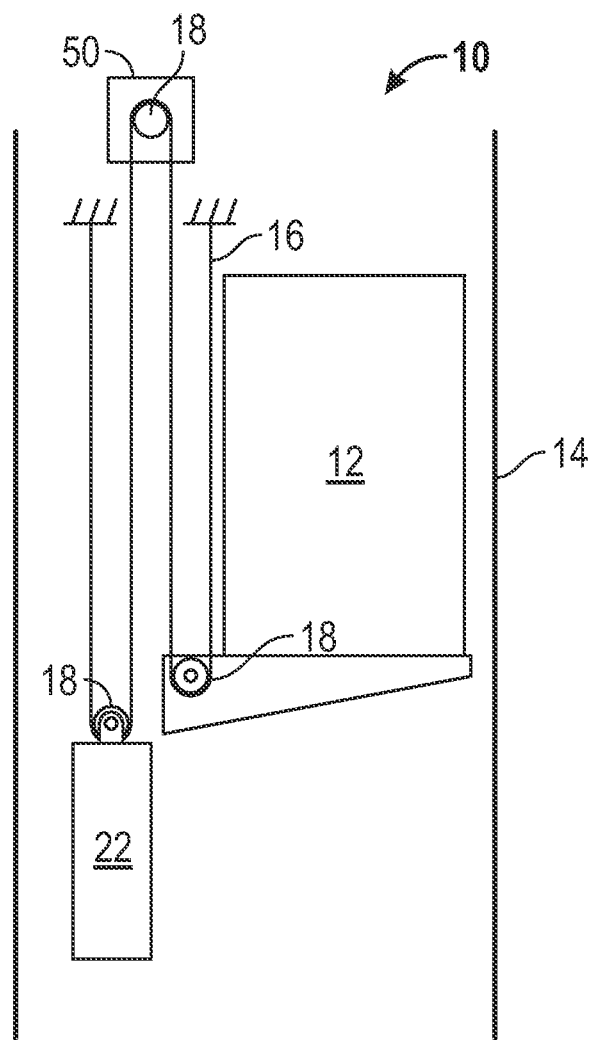
FIG. 1C is a schematic of another exemplary elevator system having a cantilevered arrangement.

Shown in FIGS. 1A, 1B and 1C are schematics of exemplary traction elevator systems 10 that could utilize the present invention. Features of the elevator system 10 that are not required for an understanding of the present invention (such as the guide rails, safeties, etc.) are not discussed herein. The elevator system 10 includes an elevator car 12 operatively suspended or supported in a hoistway 14 with one or more belts 16. The one or more belts 16 interact with one or more sheaves 18 to be routed around various components of the elevator system 10. The one or more belts 16 could also be connected to a counterweight 22, which is used to help balance the elevator system 10 and create traction.

The sheaves 18 each have a diameter 20, which may be the same or different than the diameters of the other sheaves 18 in the elevator system 10. At least one of the sheaves 18 could be a drive sheave. A drive sheave is driven by a machine 50. Movement of the drive sheave by the machine 50 drives, moves and/or propels (through traction) the one or more belts 16 that are routed around the drive sheave.

At least one of the sheaves 18 could be a diverter, deflector or idler sheave. Diverter, deflector or idler sheaves are not driven by a machine 50, but help guide the one or more belts 16 around the various components of the elevator system 10. Further, one or more of the sheaves 18, such as the diverter, deflector or idler sheaves, may have a convex shape or crown along its axis of rotation to assist in keeping the one or more belts 16 centered, or in a desired position, along the sheaves 18.

In some embodiments, the elevator system 10 could use two or more belts 16 for suspending and/or driving the elevator car 12. In addition, the elevator system 10 could have various configurations such that either both sides of the one or more belts 16 engage the one or more sheaves 18 (such as shown in the exemplary elevator systems in FIG. 1A, 1B or 1C) or only one side of the one or more belts 16 engages the one or more sheaves 18.

FIG. 1A provides a 1:1 roping arrangement in which the one or more belts 16 terminate at the car 12 and counterweight 22. FIGS. 1B and 1C provide different roping arrangements. Specifically, FIGS. 1B and 1C show that the car 12 and/or the counterweight 22 can have one or more sheaves 18 thereon engaging the one or more belts 16 and the one or more belts 16 can terminate elsewhere, typically at a structure within the hoistway 14 (such as for a machineroomless elevator system) or within the machine room (for elevator systems utilizing a machine room). The number of sheaves 18 used in the arrangement determines the specific roping ratio (e.g., the 2:1 roping ratio shown in FIGS. 1B and 1C or a different ratio). FIG. 1C also provides a cantilevered type elevator. The present invention could be used on elevator systems other than the exemplary types shown in FIGS. 1A, 1B and 1C.

Figure 2:
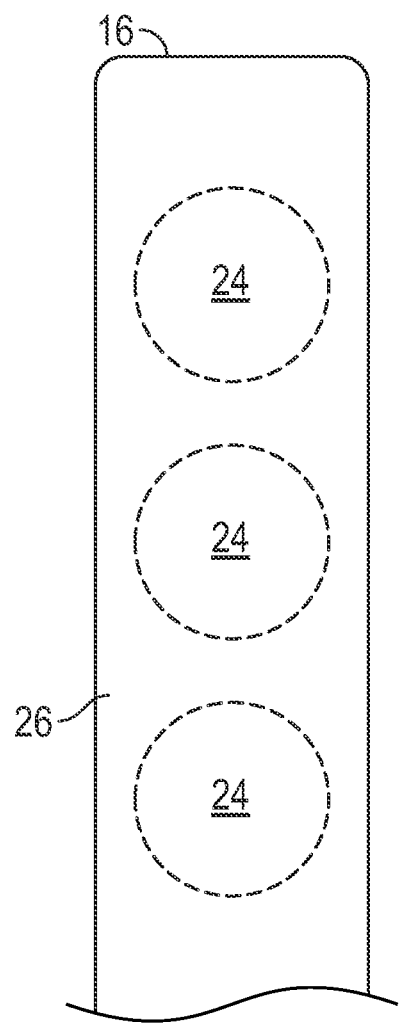
FIG. 2 is a cross-sectional view of an elevator belt.

FIG. 2 provides a schematic of an exemplary belt construction or design that could utilize the present invention. The present invention is also capable of use with coated rope. Each belt 16 can be constructed of one or more cords 24 in a jacket 26. As seen in FIG. 2, the belt 16 can have an aspect ratio greater than one (i.e. belt width is greater than belt thickness). The belts 16 can be constructed to have sufficient flexibility when passing over the one or more sheaves 18 to provide low bending stresses, meet belt life requirements and have smooth operation, while being sufficiently strong to be capable of meeting strength requirements for suspending and/or driving the elevator car 12. The jacket 26 could be any suitable material, including a single material, multiple materials, two or more layers using the same or dissimilar materials, and/or a film. In one arrangement, the jacket 26 could be a polymer, such as an elastomer, applied to the cords 24 using, for example, an extrusion or a mold wheel process. In another arrangement, the jacket 26 could be a woven fabric that engages and/or integrates the cords 24. As an additional arrangement, the jacket 26 could be one or more of the previously mentioned alternatives in combination.

The jacket 26 can substantially retain the cords 24 therein. The phrase substantially retain means that the jacket 26 has sufficient engagement with the cords 24 to transfer torque from the machine 50 through the jacket 26 to the cords 24 to drive movement of the elevator car 12. The jacket 26 could completely envelop the cords 24 (such as shown in FIG. 2), substantially envelop the cords 24, or at least partially envelop the cords 24.

Figure 3:
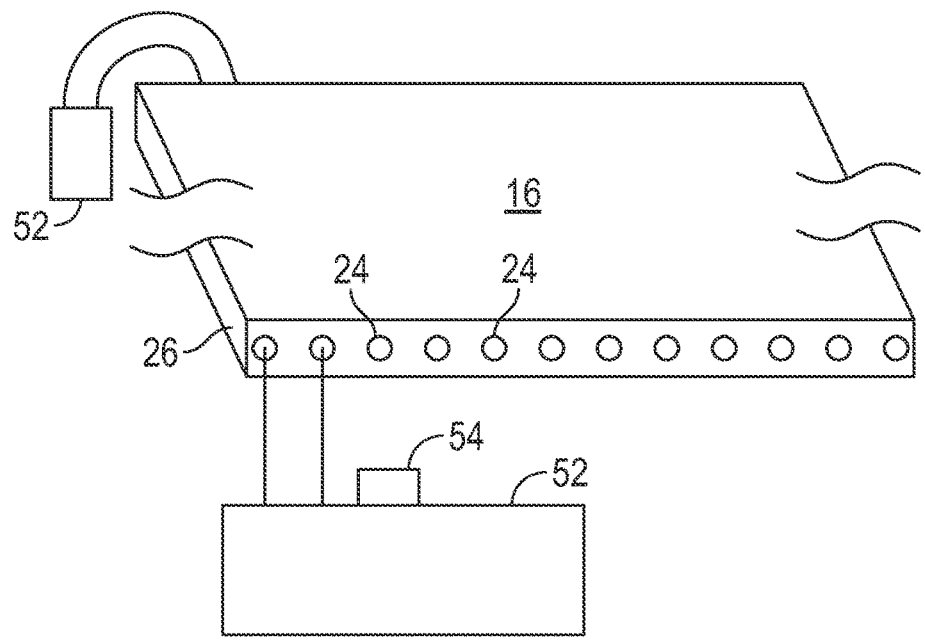
FIG. 3 is a schematic of an elevator belt wear detection unit.
Figure 3A:
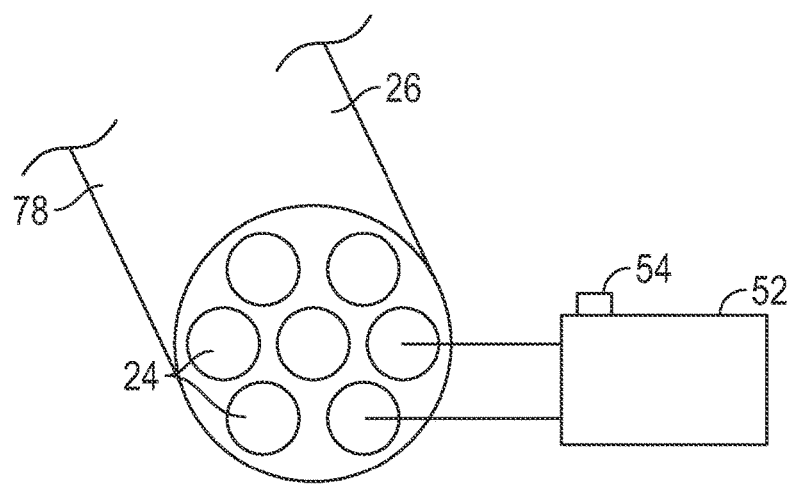
FIG. 3A is a schematic of a wear detection unit in conjunction with a coated rope.

Referring to FIG. 3, a wear detection unit 52 is electrically connected to one or more cords 24 of the belt 16. Although described below with respect to cords, the unit 52 could alternatively be electrically connected to one or more strands of the belt or rope, or to one or more wires of the belt or rope. The wear detection unit 52 is connected to belt 16 at a suitable location, for example, at an end of the belt 16 located at an upper end of the hoistway 14 (e.g. the 2:1 roping arrangements shown in FIGS. 1B and 1C). It is to be appreciated, though, that this location is merely exemplary and other locations for connecting the wear detection unit 52 to the belt 16 are contemplated within the present scope. For example, in the 1:1 roping arrangement shown in FIG. 1A, the unit 52 would need to engage the end(s) of the belt 16. During operation, an electrical current is applied through the cords 24. A resulting voltage allows for determination of an electrical resistance of the cord 24. This measured resistance is compared to an initial resistance of the cord measure during initial installation of the belts 16. A change in the electrical resistance of the cord 24, typically an increase in resistance, indicates wear of the cord 24. The change in resistance is compared to one or more thresholds, and when the threshold is exceeded, action may be taken by the elevator system 10, including but not limited to, notifying the maintenance provider, sounding of an alarm and/or stopping operation of the elevator system 10. To return the signal transmitted through the cords 24 to the wear detection unit 52, another wear detection unit 52, or other device such as a shunt connector is provided to transmit the return signal. Referring to FIG. 3A, the wear detection unit 52 may be utilized with a coated rope 78 including a plurality of cords 24 coated with a jacket 26 in a manner similar to that described herein regarding the belt 16.

Figure 4:
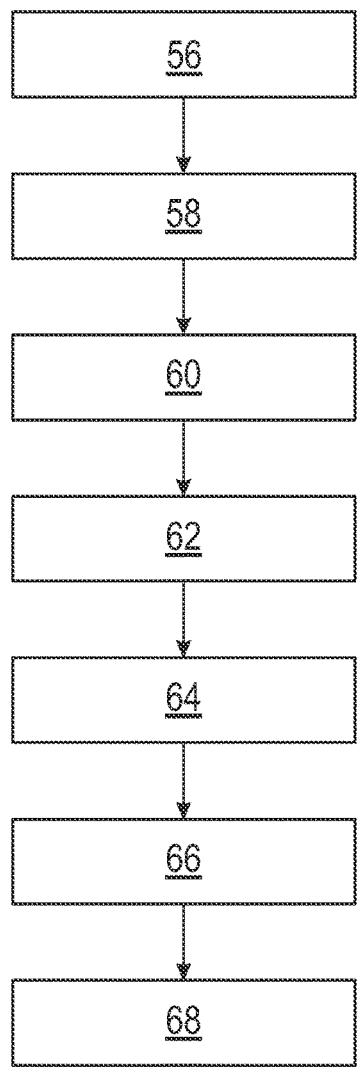
FIG. 4 is an illustration of a method for calibrating a wear detection unit.

In the wear detection unit 52, the threshold is determined or set, based on an initial measured resistance of the belt 16, and may be a percent change of the measured resistance from the initial measured resistance. The wear detection unit 52 further includes a temperature sensor 54 to measure a temperature at the wear detection unit 52 to which the initial measured resistance correlates. To more accurately determine the threshold, and thereby more accurately determine a level of wear in the cord 24, the determination of the initial measured resistance is made based upon repeated resistance measurements made periodically over an initial time period after installation. The sampling of the resistance measurements should be frequent enough to capture the normal temperature variations that occur during the course of a day, for example once per hour. The length of the initial time period used for determining the initial resistance should be long enough to capture typical variations that occur, for example six months. However, the length of the initial time period needs to be chosen so that degradation of the cord 24 is not experienced during the process. Stated differently, the time period is chosen so that the coated belt or rope still exhibits characteristics of a new coated belt or rope. An exemplary method is shown in FIG. 4.

The process begins at step 56 with installation of the coated belt or rope in elevator system 10 in the hoistway 14. The installation could be the initial coated belt or rope used in the elevator system 10 or a replacement belt or rope installed at a later time in the life of the elevator system 10. At step 58, the initial cord resistance is measured and an initial temperature is also measured by the temperature sensor 54. The initial cord resistance and initial temperature are stored in the wear detection unit 52 or other suitable location, such as in memory located off-site at the maintenance provider of the elevator system 10 at step 60. The measurement of temperature and resistance are repeated periodically as part of a calibration routine as shown at step 62. This results in a set of calibration resistances and calibration temperatures which, along with the initial cord resistance and initial temperature, populate a database of temperatures and corresponding resistances at step 64. Because the calibration routine is performed early in the service life of the belt 16, no deterioration of the belt 16 has yet occurred, so the database is, in effect, a collection of initial cord resistance values at various temperatures.

Figure 5:
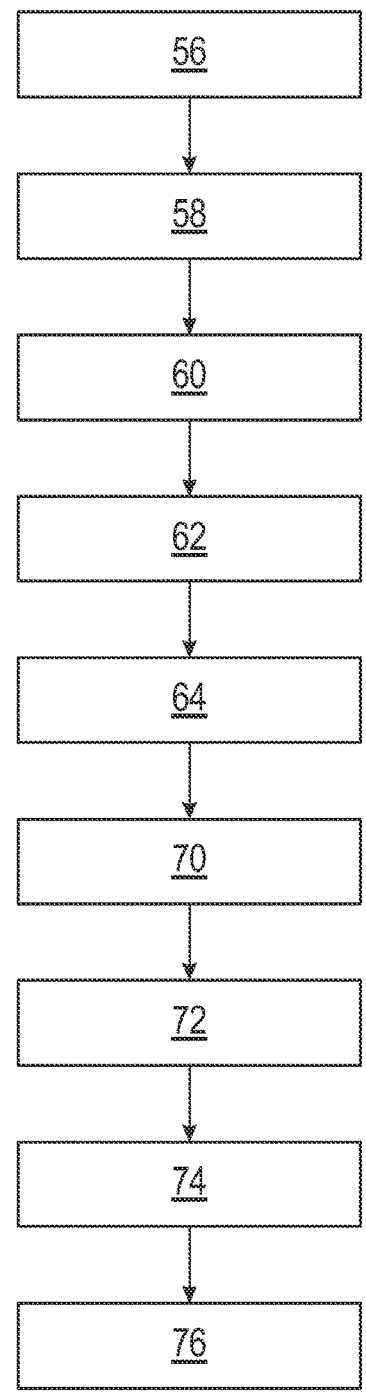
FIG. 5 is an illustration of another method for calibrating a wear detection unit.

In some embodiments, the resistance values in the database are averaged at step 66 to determine a calibrated initial resistance used in calculation of a threshold at step 68. As an example, the threshold could be 80% of calibrated initial resistance. In other embodiments, as shown in FIG. 5, the threshold is determined each time an inspection is performed at step 70. After the calibration routine is completed, an inspection temperature and an inspection resistance are measured at step 70. At step 72, the database is queried, and a calibration resistance for that particular temperature is determined at step 74. The calibration resistance is used in calculation of the threshold at step 76, to which the inspection resistance is compared.

Performing the calibration routine and utilizing temperature measurements in determination of the threshold provides a more accurate initial resistance value for determining the threshold thereby providing a more accurate determination of belt 16 condition. Further, the calibration routine allows for a better understanding of the effects of cord temperature on measured belt resistance.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A method of wear detection of a coated belt or rope of an elevator system, comprising:
   electrically connecting a wear detection unit to one or more cords, strands or wires of the coated belt or rope;
   applying an electrical current to the one or more cord, strands or wires via the wear detection unit;
   measuring an initial electrical resistance of the one or more cords, strands or wires of the coated belt or rope based on the applied electrical current;
   calibrating the initial electrical resistance by:
      repeating the measuring of initial electrical resistance;
      populating a database with the measured initial electrical resistance values; and
      determining a true initial resistance from the population of initial electrical resistances;
   calculating a threshold value based on the true initial resistance;
   measuring the electrical resistance of the one or more cords, strands or wires subsequent to the determination of the true initial resistance;
   comparing the subsequent measured value of electrical resistance of the one or more cords, strands or wires of the coated belt or rope to the threshold, a difference of electrical resistance between the subsequent measured value of electrical resistance and the threshold indicative of wear of the coated belt or rope; and
   taking action when the subsequent measured value of electrical resistance exceeds the threshold, the taking action including stopping operation of the elevator system.

2. The method of claim 1, wherein the true initial resistance is determined by computing an average of the population of initial electrical resistances.

3. The method of claim 1, wherein the initial resistance measurement is repeated at an interval sufficient to allow for coated belt or rope temperature variation throughout a course of a day.

4. The method of claim 3, wherein the interval is about an hour.

5. The method of claim 1, wherein the initial resistance measurement is repeated over an operating period such that no degradation of the cords, strands or wires is not experienced during repetition of the initial resistance measurement.

6. The method of claim 5, wherein the operating period is about six months.

7. The method of claim 1, further comprising:
   measuring an initial temperature at the wear detection unit at the time of measuring the initial electrical resistance
   repeating the initial temperature measurement along with repeating the measuring of initial resistance;
   populating the database with the measured initial temperatures correlated to the measured initial resistance values.

8. The method of claim 7, further comprising:
   subsequently measuring electrical resistance of one or more cords, strands or wires of the coated belt or rope and temperature after populating the database;
   selecting the true initial electrical resistance corresponding to the measured temperature from the database; and
   comparing the measured electrical resistance after populating the database to the threshold.

9. A monitoring system for a coated belt or rope having one or more cords, strands and/or wires, comprising:
   a wear detection unit for engaging the one or more cords, strands or wire of the coated belt or rope and configured to measure electrical resistance thereof;
   a temperature sensor configured to measure temperature at the wear detection unit; and
   a database configured to store electrical resistance and corresponding temperature measurements;
   wherein the wear detection unit repeatedly measures an initial electrical resistance, and the temperature sensor repeatedly measures an initial temperature, the initial electrical resistance measurements and initial temperatance by selecting a true initial electrical resistance corresponding to a measured temperature subsequent to the initial temperature measurement from the database.

10. The monitoring system of claim 9, in combination with an elevator system having one or more coated belts or ropes each having one or more cords, strands and/or wires.

\* \* \* \* \*